United States Patent
Lin et al.

(10) Patent No.: US 6,864,971 B2
(45) Date of Patent: Mar. 8, 2005

(54) SYSTEM AND METHOD FOR PERFORMING OPTICAL INSPECTION UTILIZING DIFFRACTED LIGHT

(75) Inventors: YouLing Lin, Richardson, TX (US); A. Kathleen Hennessey, Richardson, TX (US); Yongqiang Liu, Plano, TX (US); Yonghang Fu, Plano, TX (US); Masami Yamashita, Kumamoto (JP); Ichiro Shimomura, Kikuyo-machi (JP)

(73) Assignee: ISOA, Inc., Richardson, TX (US)

( * ) Notice: Subject to any disclaimer, the term of this patent is extended or adjusted under 35 U.S.C. 154(b) by 328 days.

(21) Appl. No.: 10/094,119
(22) Filed: Mar. 8, 2002

(65) Prior Publication Data
US 2002/0140930 A1 Oct. 3, 2002

Related U.S. Application Data
(60) Provisional application No. 60/278,961, filed on Mar. 27, 2001.

(51) Int. Cl.[7] .............................................. G01N 21/88
(52) U.S. Cl. ................................ 356/237.4; 356/237.5; 356/237.2; 250/559.44
(58) Field of Search ........................... 356/237.2, 237.4, 356/237.5, 600, 636; 250/559.44

(56) References Cited

U.S. PATENT DOCUMENTS

| | | | |
|---|---|---|---|
| 4,595,289 A | 6/1986 | Feldman et al. ............ 356/237 |
| 5,046,847 A | 9/1991 | Nakata et al. .............. 356/338 |
| 5,264,912 A * | 11/1993 | Vaught et al. ........... 356/237.5 |
| 5,488,476 A * | 1/1996 | Mansfield et al. .......... 356/512 |
| 5,818,576 A | 10/1998 | Morishige et al. .......... 356/237 |
| 5,822,055 A | 10/1998 | Tsai et al. .................... 356/237 |
| 6,091,846 A | 7/2000 | Lin et al. ..................... 382/145 |
| 6,104,481 A * | 8/2000 | Sekine et al. ............ 356/237.5 |
| 6,452,671 B1 * | 9/2002 | Uda et al. ................. 356/237.2 |
| 6,590,656 B2 * | 7/2003 | Xu et al. ..................... 356/369 |
| 6,654,113 B2 * | 11/2003 | Fukazawa et al. ....... 356/237.4 |

* cited by examiner

Primary Examiner—Richard A. Rosenberger
Assistant Examiner—Vincent P. Barth

(57) ABSTRACT

A system and method for performing optical inspection of structures on the surface of a semiconductor wafer. The wafer surface is illuminated with a polychromatic light source. A multiple-charged couple-device (CCD) camera is positioned to capture light diffracted by the structures on the wafer surface at the first order of diffraction. The captured light is then separated into a plurality of component wavelengths which are directed onto the CCDs. A digital filter creates a plurality of digitized diffractive images of the wafer surface at different component wavelengths. The diffractive images may be integrated and analyzed to detect defects in the structures, or may be, analyzed individually. An image at a particular wavelength may be selected and analyzed by using the known grating pitch of the structures to calculate the wavelength.

22 Claims, 4 Drawing Sheets

SYSTEM AND METHOD FOR PERFORMING OPTICAL INSPECTION UTILIZING DIFFRACTED LIGHT

PRIORITY STATEMENT UNDER 35 U.S.C. § 119(e) & 37 C.F.R. § 1.78

This nonprovisional application claims priority based upon the prior U.S. provisional patent application No. 60/278,961 entitled, "*Method of performing Optical Inspection*", filed Mar. 27, 2001 in the names of A. Kathleen Hennessey, YouLing Lin, Yongqiang Liu, Yonghang Fu, Yamashita Masami, and Ichiro Shimomura.

BACKGROUND OF THE INVENTION

1. Technical Field of the Invention

This invention relates to optical inspection systems. More specifically, and not by way of limitation, the invention is directed to a system and method for automated optical inspection of regularly-patterned production surfaces, such as those on semiconductor wafers, using diffracted light.

2. Description of Related Art

Optical inspection of articles of manufacture, either finished or in-process, may range from simple visual inspection to sophisticated computer-assisted inspection. Automated inspection is increasingly valuable as equipment and techniques improve because it is fast, reliable, and can frequently detect production defects that cannot be easily perceived by the unaided human eye.

This is true in the case of the in-process inspection of semiconductor wafers. Semiconductor wafers are manufactured in stages, with each stage representing the development of a new layer, or set of surface structures that form a functional part of the electronic devices that will populate the wafer when it is finished. The structures of each stage are formed by selectively etching away or treating carefully selected areas of the surface. The selection of areas to be etched or treated is often accomplished by covering the remaining area with a protective material called photoresist.

The photoresist is first applied evenly to the entire wafer surface, then selectively exposed to light emitted through a mask. This changes the nature of the exposed area so that it becomes, for example, more or less soluble. Then during development the exposed areas are either retained or washed away (depending on the type of photoresist used), leaving a pattern of resist structures that will protect We wafer surface under them as the remainder of the surface is altered. During the process of etching, for example, unprotected areas are removed to a certain depth, perhaps to be filled later or otherwise treated. The protective photoresist is then removed, leaving only the desired surface configuration. The next stage can then be prepared for treatment and the process repeated until the desired surface structures have been completely formed.

Frequent inspections of the wafer surface are desirable during the production process, especially at the point where photoresist structures have been formed. Although many types of defects can be repaired, the photoresist is relatively easily removed and reapplied, so it is most advantageous to detect defects in it, rather than etching an improperly treated wafer that would be more difficult and expensive to repair.

Wafers in the process of manufacture can, of course, and sometimes are visually inspected for defects. Generally, however, an automated inspection system is used In such systems, some form of electromagnetic energy, often but not always visible light, is directed at the surface to be inspected. The image created by the light reflecting from the surface is then captured and translated into digital form for processing by a computer.

The surface-image data may, for example, be analyzed to determine if unusual or tell-tale patterns are present—those commonly associated with certain kinds of defects. In one such technique, called image decomposition, surface structures are traced and described in terms of grammars composed of units called primitives. One such technique is explained in detail in U.S. patent application Ser. No. 09/074,301, entitled SYSTEM AND METHOD OF OPTICALLY INSPECTING MANUFACTURED DEVICES, filed May 6, 1998, a continuation in-part of U.S. patent application Ser. No. 08/867,156, which issued on Jul. 18, 2000 as U.S. Patent Ser. No. 6,091,846, entitled METHOD AND SYSTEM FOR ANOMALY DETECTION, both of which are by reference incorporated herein in their entirety. In more sophisticated systems, the images associated with each inspection are classified, stored, and indexed for later use. Comparisons may be made to detect errors in the defect-detection process itself and to analyze the manufacturing process in order to determine, if possible, the root cause of frequently discovered defects in the hope of minimizing the occurrence of similar defects in the future.

In some instances, capturing an image of light reflected specularly from the wafer surface is inadequate for efficient and comprehensive defect detection. It has been found, for example, that defects such as focus offset, or defocus due to the presence of stray particles, errors in wafer development, etching or stripping, or to insufficient developer, are detectable by examining the light diffracted from the production surface. When, as is the case with a properly-constructed semiconductor wafer, an object's surface features are small and sufficiently uniform so as to form a regular pattern that amounts to or approximates a diffraction (or, more properly, a reflection) grating, an analysis of the diffracted light is also useful.

The utilization of diffracted light, however, somewhat complicates the inspection process. For example, when monochromatic light is directed at a particular area on the wafer surface for which the grating pitch (i.e., distance between the regular surface features) is known, it is possible to predict the angle of first- (or other-) order diffraction. Since the angle of diffraction is a function of the grating pitch, however, the camera or other image-capturing device used must be repositioned each time the grating pitch changes.

In other words, to accommodate the varying surface patterns (i.e., grating pitches) commonly found on semiconductor wafers, either the camera or the light source must be relocated. This is due to the fact that each different grating pitch will yield a different angle of diffraction relative to the angle of incidence. Of course, the orientation of the wafer could be adjusted according to the expected diffraction angle, but such adjustments are less than desirable because they are more cumbersome and introduce a greater risk of error.

What is needed is a way to take advantage of the diffraction effect during the automated inspection of semiconductor wafers without having to make continual adjustments to the geometry of the inspection system. The present invention provides such a system and method.

SUMMARY OF THE INVENTION

In one aspect, the present invention is directed to: a method of performing optical inspection of structures on the surface of a semiconductor wafer. The wafer surface is illuminated with a polychromatic light source. This is followed by capturing light diffracted by the structures on the wafer surface at an angle corresponding to the first-order of diffraction, and separating the captured light into a plurality of component wavelengths. A plurality of diffractive images of the wafer surface are then created, each image being created at a different component wavelength. The diffractive images are then analyzed to detect defects in the structures. An image at a particular wavelength may be selected and analyzed by using the known grating pitch of the structures to calculate the wavelength. As the grating pitch changes in different areas of the wafer surface, a different wavelength is calculated, and a different image at the new wavelength is selected and analyzed.

In another aspect, the present invention is directed to a system for performing optical inspection of structures on a surface of a semiconductor wafer. The system includes means for illuminating the wafer surface with a polychromatic light; means for capturing light diffracted by the structures on the wafer surface; and means for separating the captured light into a plurality of component wavelengths. The system also includes means for creating a plurality of diffractive images of the wafer surface, each image being created at a different component wavelength; and means for analyzing the diffractive images to detect defects in the structures. The means for capturing the diffracted light may be a multiple-charged-couple-device (CCD) camera which may be mounted in a position to capture light at the angle of first-order diffraction.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF EMBODIMENTS

The present invention is directed to a system and method for using the diffraction effect of electromagnetic energy in performing an automated optical inspection of the surface of an object. It is applicable for inspection of any surface having surface structures that, when properly constructed, form a regular pattern or patterns whose pattern elements approximate a reflection grating. As mentioned above, one such surface is the in-process manufactured surface of a semiconductor wafer. The present invention will hereafter be described in an embodiment suitable for wafer inspection, though it should be noted that it is also useful for inspecting a variety of similar surfaces and no limitation to the contrary is intended.

Figure 1A:
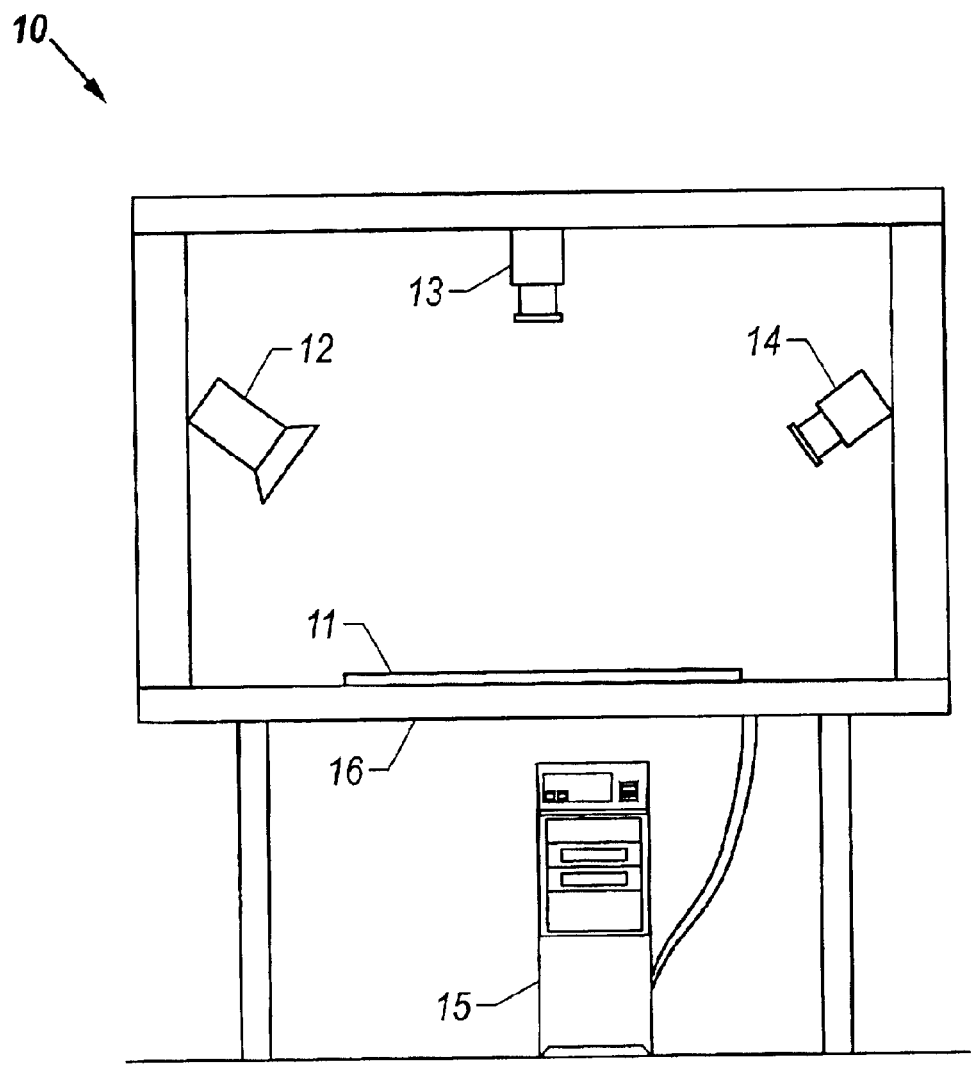
FIG. 1A is a front elevation view of an optical inspection system configured to inspect a semiconductor wafer in accordance with the preferred embodiment of the present invention.

FIG. 1A is a front elevation view of an optical inspection system 10 configured to inspect a semiconductor wafer 11 in accordance with the preferred embodiment of the present invention. The system 10 may be utilized to detect and locate photoresist anomalies. The anomaly detection/location system 10 comprises a light source 12, an overhead image capturing device 13, a diffractive image capturing device 14, a control computer 15 and a wafer support stand 16 which holds the semiconductor wafer 11. The light source may emit light or energy on the surface of the wafer utilizing, for example, laser light, X-rays, ion beams, electrons, or light in the infrared, ultraviolet, or visible spectrum.

The efficiency of the present invention and its ability to detect structure edges, such as photoresist island edges, is largely dependent upon the production of crisp, sharp component edges by the overhead image capturing device 13, and to precisely measure the angle of diffraction by the diffractive image capturing device 14. Therefore, the light source 12 is preferably a coherent light source which minimally diffuses the emitted light. The overhead image capturing device 13 is preferably a single line-scan or area-scan overhead camera. The diffractive image capturing device 14 is preferably a multiple-CCD (charged-couple device) camera that is capable of separately capturing different wavelengths of the light propagating from the surface. A suitable image capturing device is the XC003 3CCD Area-Scan Color Camera available from the Sony Corporation.

Figure 1B:
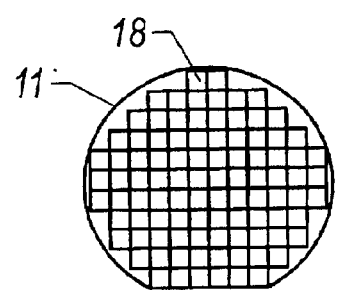
FIG. 1B is a top plan view of the semiconductor wafer under inspection illustrating a plurality of dice on the surface thereof.

FIG. 1B is a top plan view of the semiconductor wafer 11 illustrating a plurality of dice such as die 18 on the surface thereof. In this embodiment, the wafer 11 to be inspected is placed in the inspection stand 16 which is part of the optical inspection system 10. The inspection stand not only provides a secure support for the wafer, but supports the cameras and light source as well. The stand may also support a number of optical lenses and mirrors to focus and direct light as required for a particular inspection. It is here that the Wafer is illuminated so that an image can be captured, then digitized, stored, and analyzed as desired.

In one embodiment of the present invention, the light source emits polychromatic white light directed at the surface of the wafer at a predetermined angle to the normal axis. The image-capturing device is a multiple-CCD camera that is capable of separately capturing different wavelengths of the light propagating from the surface. More specifically, the camera separately captures light in a plurality of wavelength ranges, for example, the red, blue, and green portions of the visible-light spectrum. Note that these spectra may not be visibly divided as they enter the camera; the separation is done internally. Note also that the image-capturing device will for convenience be referred to throughout as a camera, but it can be any suitable device for capturing the reflected or diffracted light (including any form of electromagnetic radiation) in accordance with the present invention.

Due primarily to the different wavelengths producing them, the separately captured images are somewhat different from each other. One of the plurality of separate images will be the best one for use in determining if a defect exists; some defects may even escape detection in one image while still being detectable in another. It is difficult to predict in advance, however, which image will be the most useful, so preferably each of the images should be analyzed for each wafer.

In a preferred embodiment, the present invention takes advantage of electromagnetic-energy diffraction phenomena. The regular pattern formed by developed photoresist structures on the wafer surface form a reflection grating that results in diffraction as well as specular reflection. Certain types of defects become more easily detectable through an examination of this diffracted light. Diffracted light phenomena can be described by the relationship:

$$m\lambda = d(\sin \theta_i + \sin \theta_m) \quad (1)$$

where light of wavelength λ striking the grating (i.e. the wafer surface-structures) having a pitch d at angle of incidence $\theta_i$ exhibits a diffraction beam propagating at an angle $\theta_m$, m signifying the order of diffraction. Where, as is done with existing systems, a monochromatic light of known wavelength is used, the diffraction angle $\theta_m$ is calculated and a camera is appropriately placed to capture the desired image.

The disadvantage of such a system is that in order to inspect wafer surfaces when the grating pitch (surface structure separation) varies, as it generally does, multiple cameras must be used to accommodate the various first-order diffraction angles that will result, or a camera must be moved from one location to another. Failing one of those measures, the wavelength of the monochromatic light or its angle of incidence must be changed (by moving the source or the target wafer) so as to produce a diffraction angle that can be accommodated by the existing camera configuration.

Any of these adjustments introduce an undesirable risk of inaccuracy into the defect detection process. Accordingly, the system and method of the present invention use a fixed configuration. As used herein, fixed does not mean unadjustable, however, but rather that in ordinary operation the position of the light source and image-capturing device do not have to be adjusted to accommodate varying wafer structures. Increased accuracy and efficiency result.

In a preferred embodiment of the present invention, the wafer is illuminated using white light, which contains all wavelengths of visible light. Alternately, a different illumination spectrum may be used, even one that is non-continuous or created by more than one different source, or one source optically divided into separate sources. (There may be reasons why this is desirable that are not directly related to practicing the present invention.)

The diffraction-effect camera is preferably positioned so that it can capture the first-order diffraction light formed by a wide range of grating pitches. This is possible because the light entering the diffraction-effect camera is separated into its component images. Each image represents a distinct range of wavelengths λ that are analyzed as described below.

In an alternate embodiment, the overhead image-capturing device 13 may also be used in the standard fashion, that is, for capturing a full-spectrum image of the illuminated wafer for analysis. The overhead camera image, however, is not necessary to the present invention except to the extent that the data extracted from the diffraction-effect camera is analyzed in combination with it, a practice that may in some circumstances be desirable. In yet another embodiment, the multiple-CCD camera images can be recombined in a digitizer to form a full-spectrum image. The full-spectrum image can be used for other forms of inspection, or in conjunction with the diffraction-effect analysis as described herein.

Figure 2:
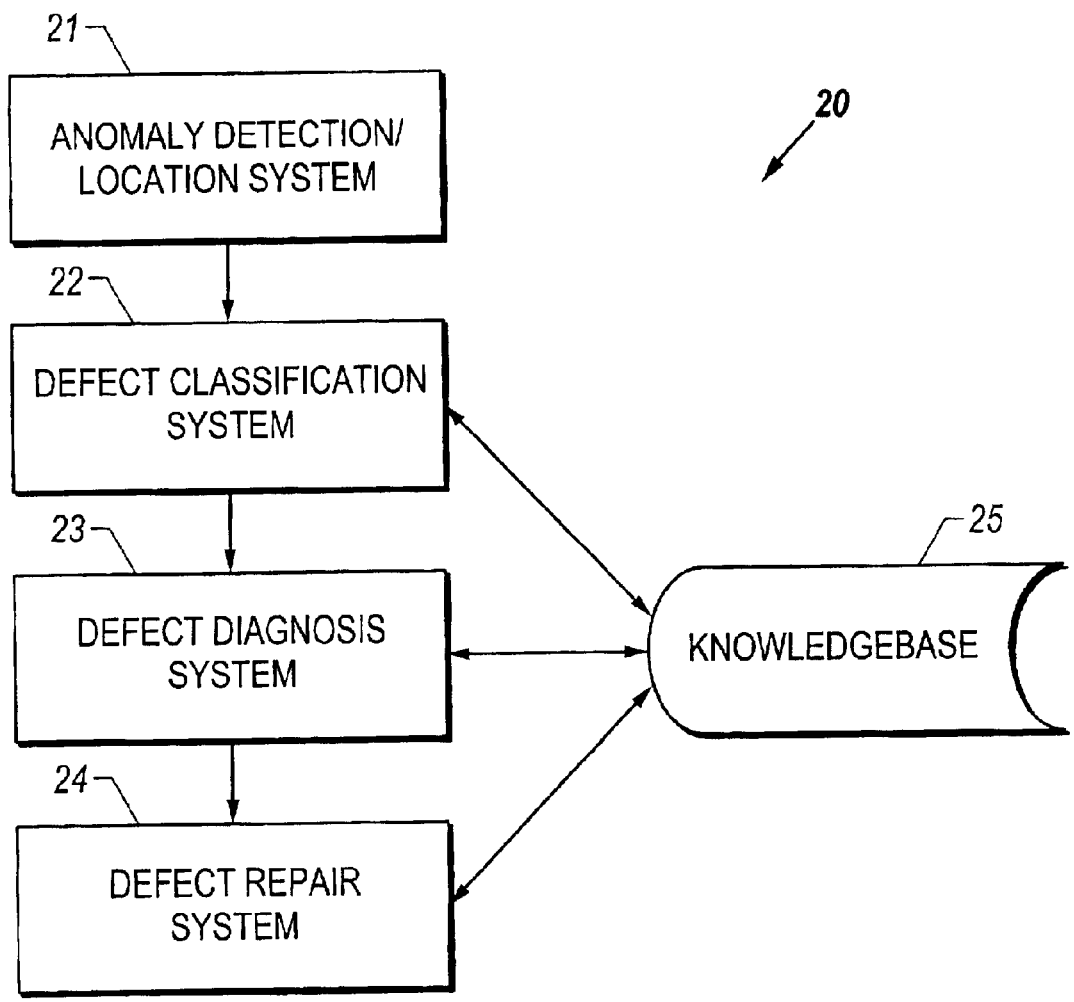
FIG. 2 is a block diagram illustrating the interrelations of subsystems in an Anomaly Detection and Correction System (ADCS) in accordance with an embodiment of the present invention.

FIG. 2 is a block diagram illustrating the interrelations of subsystems in an Anomaly Detection and Correction System (ADCS) 20, typical of one that may be used in analyzing image data in accordance with an embodiment of the present invention. In the ADCS, there is an anomaly detection/location system 21, a defect classification system 22, a defect diagnosis system 23, a defect repair system 24, and a knowledgebase 25. The anomaly detection/location system 21 pinpoints the location of the defects. Once any defects are located, the defect classification system 22 identifies and uses recorded characteristics of defect images in order to determine the type (or types) of defect detected. Once the defect type is determined, the defect diagnosis system 23 matches the defect types stored in the knowledgebase 25 to a database of known defect causes in order to judge the cause of the defect. After the cause of the defect is predicted, the defect repair system 24 uses information stored in the knowledgebase to determine if the defect is correctable, and, if so, directs the repair operation.

Figure 3:
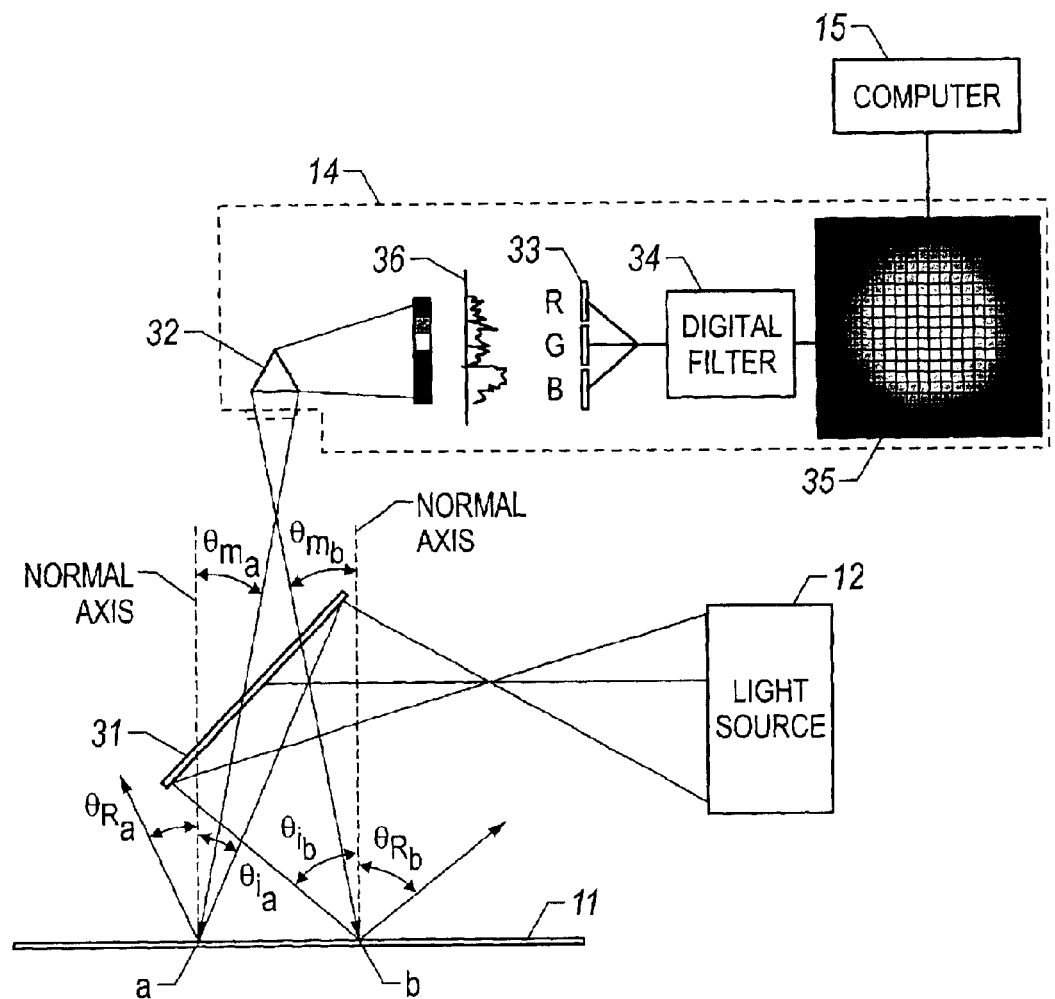
FIG. 3 is a simplified diagram of the lighting and image-capturing system of the preferred embodiment of the present invention.

FIG. 3 is a simplified diagram of the lighting and image-capturing system of the preferred embodiment of the present invention. The light source 12 may emit polychromatic light for illumination of the surface to be inspected, here semiconductor wafer 11. The light may be redirected toward the surface of the wafer using a semi-reflective mirror referred to as a 50/50 beam splitter 31. The light strikes the surface of the wafer at an angle $\theta_i$ incident to the normal axis. FIG. 3 is labeled to show the angles of incidence and $m^{th}$ order diffraction corresponding to two points (a and b) on the wafer surface. Light from the surface is reflected specularly at an equal angle, $\theta_r$ (for clarity, this angle is shown at only two reflection points). Due to the diffraction effect created by the wafer surface structures, $m^{th}$ order diffraction beams also propagate away from these points at an angle $\theta_m$.

Some (but not necessarily all) of the diffracted light is captured by the multiple-CCD camera 14. The camera includes a prism 32 that separates the incoming light into its component wavelengths. The three CCDs 33 of the camera capture the light from each of three separate spectra (shown in FIG. 3 as red, green, and blue) to produce three separate images.

The three captured images (and, in accordance with the present invention, there could also be two, or more than three) are digitized by a digital filter 34 to form digital images which may be transmitted to the computer 15 for storage and analysis. Alternatively, the images may be integrated to form a full-spectrum digital image 35 which may be transmitted to the computer 15 for storage and analysis. Optionally, after the prism 32 separates the incoming light into its component wavelengths, a line sensor 36 may be utilized to: detect as much of the spectrum of light emanating from the prism as is desired, providing the ability to analyze the images of many, potentially hundreds, of different wavelengths.

Figure 4:
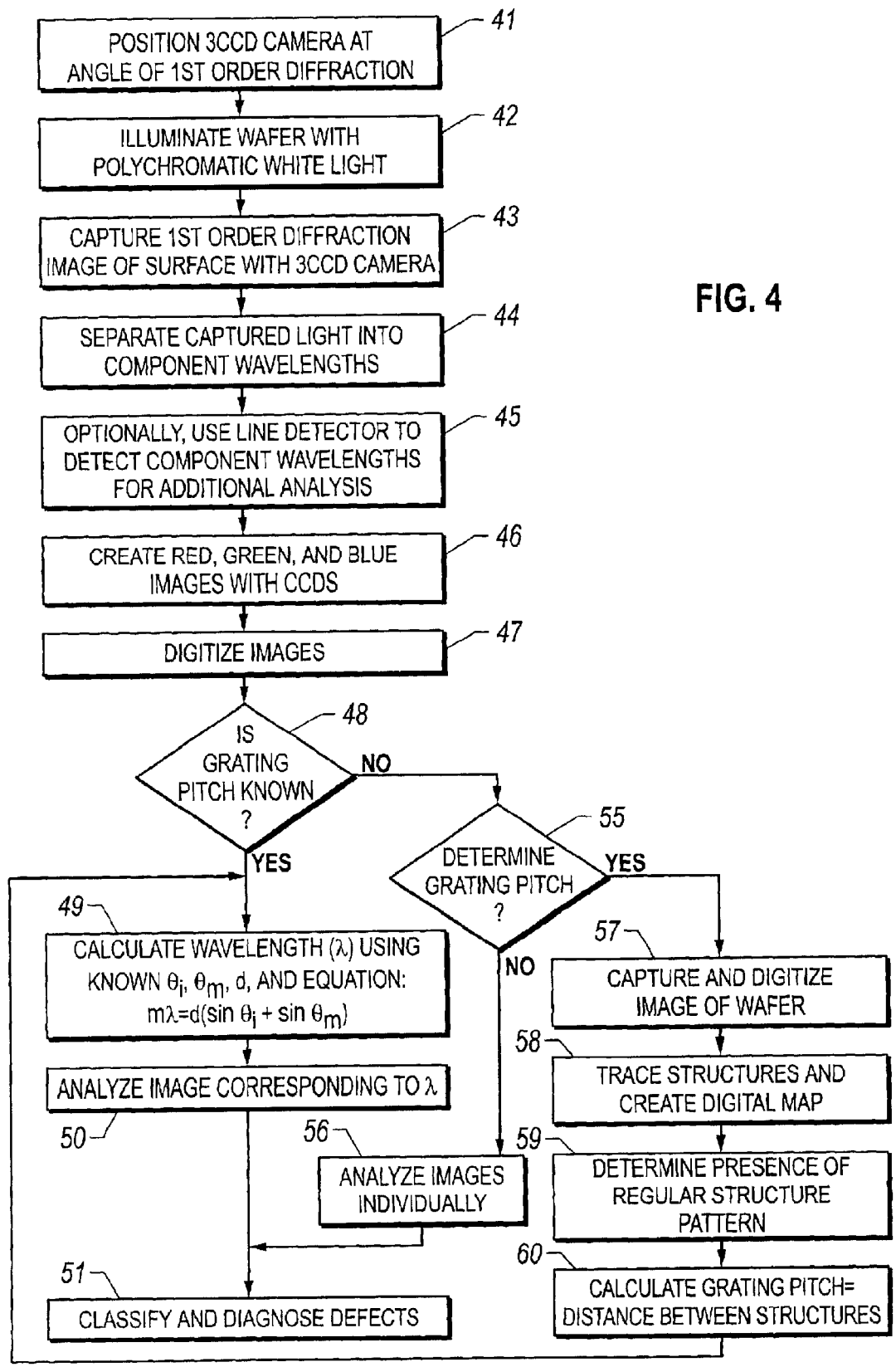
FIG. 4 is a flow chart of the steps of one embodiment of the method of the present invention.

FIG. 4 is a flow chart of the steps of one embodiment of the method of the present invention. At step 41, the 3CCD camera 14 is positioned at the angle of first order diffraction. At step 42, the wafer surface is illuminated, preferably with polychromatic white light. At step 43, the first order diffraction image of the surface is captured by the 3CCD camera, and at step 44, the prism 32 separates the captured light into its component wavelengths. At step 45, the line detector 36 may optionally be utilized to detect as much of the spectrum of light emanating from the prism as is desired, providing the ability to analyze the images of many, potentially hundreds, of different wavelengths. At step 46, three CCDs 33 of the camera capture the light from the red, green, and blue spectra to produce three separate images, which are digitized at step 47.

In order to take advantage of the diffraction effect, the grating pitch (d) created by the surface structures for an area of interest is used in equation (1), along with the known angle of incidence and diffraction (the light source and the camera being fixed) to calculate a wavelength λ. The grating pitch is the distance between regularly repeating surface structures. Thus, at step 48 it is determined whether the grating pitch is known. If so, the wavelength λ is calculated at step 49. At step 50, the image corresponding to the calculated wavelength is then analyzed, assuming that the wavelength falls within the ranged of one of the captured images. While the proper wavelength will generally fall within the captured range, it is not a requirement of the present invention that all conceivable surface-structure configurations yield a useful diffraction image. If none is found, then in that event a secondary inspection method may be employed. At step 51, the defect classification system 22, defect diagnosis system 23, and the knowledgebase 25 (FIG. 2) are used to classify and diagnose the defects detected and located in the analyzed image.

If the grating pitch is not known at step 48, the process moves to step 55 where the grating pitch may be determined, if desired. In an alternate embodiment in which the grating pitch is not desired, the wavelength calculation need not be performed. As it is known that diffracted light may be used to detect certain defects (for example, defocus defects), the multiple separately-captured images produced by varying energy wavelengths (or spectra) can simply be viewed or analyzed individually at step 56 to determine if any of them shows the presence of a defect. In this embodiment, of course, the grating pitch need not be known because the wavelength or angle of diffracted light need not be calculated. A defect exposed in one of the images can be addressed appropriately regardless of the wavelength used to detect it. Of course, this embodiment is not mutually exclusive relative to those for which the calculations are performed. A combination of these methods may also be utilized.

If the grating pitch is desired at step 55, the process moves to step 57 where, in yet another embodiment, the inspection system captures a standard full-spectrum image of the entire wafer according to existing methods. The captured image is digitized and preferably stored in a database. At step 58, using a technique such as image decomposition, the structures on the surface are traced so that a digital map of the surface structures is developed, which is also storied in the database. This technique is explained more fully in U.S. patent application Ser. No. 08/867,156, and U.S. Patent Ser. No. 6,091,846, cited above. Note, however, that as used in this disclosure .the term gin "image" does not imply a particular data structure, but instead refers to the set of data corresponding to a desired wavelength or spectra regardless of form, as long as it is in a form suitable for analysis according to the present invention.

At step 59, the captured surface may be divided into a predetermined number of areas, and the structure map of each area is analyzed to determine if the area contains a regular structure pattern amenable to diffraction analysis. If so, the distance between the pattern elements is calculated at step 60. The process then returns to step 49 where this value is used as the grating pitch (d) of equation (1). A wavelength μ may then be calculated using this pitch, given the known angle of incidence (from the fixed light source), and angle of diffraction (associated with the orientation of the diffraction effect camera). Again, preferably first-order diffraction is used in the calculation but second-order, third-order, etc., diffraction may be used as well. The particular separately-captured image, having within its range the calculated wavelength, is examined for defects in the area at issue, according to the process outlined above (again assuming the calculated wavelength corresponds to one within the range of the diffraction-effect camera being utilized.)

If more than one camera or light source is available for use, of course, the process may also include the steps of determining which ones to use for a particular area of the surface. Alternatively, a determination to use more than one source/camera combination may be made. Note that depending on these factors, the inspection may be made as a series of diffraction-inducing illuminations, but may also be made in one illumination step, with the proper wavelength being determined, for example, from the full-spectrum captured image.

In the embodiment described above, the surface portions or areas used for structural grating-pitch determination were preselected, based, for example, on the desired surface-structure configuration. Alternately, the structure map of the captured surface-image can be analyzed, and a division into areas of different pitch may be determined based on this analysis. A predetermined degree of tolerance may be utilized in this case to ensure that the surface is not needlessly divided. Each area is then analyzed as described above, that is, the appropriate wavelength for obtaining a first-(or other-) order diffraction image is calculated and then the defect determination is made. As should be apparent, an advantage of the present invention is manifest where a single polychromatic illumination can be made useful for performing a diffraction analysis on a number of areas that might otherwise require some adjustment of the physical equipment or specimen.

It is thus believed that the operation and construction of the present invention will be apparent from the foregoing description. While the method, apparatus and system shown and described has been characterized as being preferred, it will be readily apparent that various changes and modifications could be made therein without departing from the scope of the invention as defined in the following claims.

What is claimed is:

1. A method of performing optical inspection of structures on a surface of a semiconductor wafer, comprising the steps of:

illuminating the wafer surface with a polychromatic light source;

capturing light diffracted by the structures on the wafer surface;

separating the captured light into a plurality of component wavelengths;

creating a plurality of diffractive images of the wafer surface, each image being created at a different component wavelength; and analyzing the diffractive images to detect defects in the structures.

2. The method of performing optical inspection of claim 1 wherein the step of illuminating the wafer surface includes illuminating the wafer surface with a polychromatic white light.

3. The method of performing optical inspection of claim 2 wherein the step of capturing light diffracted by the structures includes capturing the light at a first-order diffraction angle utilizing a multiple-charged-couple device (CCD) camera having a plurality of CCDs that capture light in a plurality of wavelength ranges.

4. The method of performing optical inspection of claim 3 wherein the step of capturing the light utilizing a multiple-CCD camera includes capturing the light utilizing a multiple-CCD camera having three CCDs that capture light in the red, green, and blue wavelength ranges of the visible light spectrum.

5. The method of performing optical inspection of claim 4 wherein the step of creating a plurality of diffractive images includes the steps of:

digitizing the light that is captured by the CCDs in the red, green, and blue wavelength ranges; and creating digitized diffractive images of the wafer surface at each of the red, green, and blue wavelength ranges.

6. The method of performing optical inspection of claim 5 wherein the structures on the surface form a grating pattern having a grating pitch, and the method further comprises the steps of:

determining whether the grating pitch is known; and if the grating pitch is not known, analyzing the digitized diffractive images individually to detect defects in the structures.

7. The method of performing optical inspection of claim 5 wherein the structures on the surface form a grating pattern having a grating pitch, and the method further comprises the steps of:

determining whether the grating pitch is known;

if the grating pitch is known, calculating a wavelength of the diffracted light; and analyzing the digitized diffractive image corresponding to the calculated wavelength to detect defects in the structures.

8. The method of performing optical inspection of claim 5 wherein the structures on the surface form a grating pattern having a grating pitch, and the method further comprises the steps of:

determining whether the grating pitch is known;

if the grating pitch is not known, determining the grating pitch;

calculating a wavelength of the diffracted light; and analyzing the digitized diffractive image corresponding to the calculated wavelength to detect defects in the structures.

9. The method of performing optical inspection of claim 8 wherein the step of determining the grating pitch includes the steps of:

capturing a full-spectrum image of the wafer surface;

creating a digital map of the structures on the surface; and calculating a distance between the structures equivalent to the grating pitch.

10. The method of performing optical inspection of claim 9 wherein the step of creating a digital map of the structures on the surface includes the steps of:

dividing the wafer surface into a predetermined number of areas; and creating a digital map of the structures in each area of the surface.

11. The method of performing optical inspection of claim 1 further comprising, after the step of separating the captured light into a plurality of component wavelengths, the steps of:

utilizing a line detector to detect the component wavelengths across the polychromatic light spectrum; and identifying wavelengths of interest for creating and analyzing digital diffractive images.

12. The method of performing optical inspection of claim 1 wherein the step of analyzing the diffractive images to detect defects in the structures includes the steps of:

integrating the diffractive images to form a full-spectrum digital image; and analyzing the full-spectrum digital image to detect defects in the structures.

13. The method of performing optical inspection of claim 1 further comprising comparing the detected defects to defect types stored in a knowledgebase to classify the defects.

14. The method of performing optical inspection of claim 13 further comprising the steps of:

storing causes of particular defect types in the knowledgebase; and diagnosing the cause of the detected defects by associating the determined defect types with the causes stored in the knowledgebase.

15. A system for performing optical inspection of structures on a surface of a semiconductor wafer, comprising:

means for illuminating the wafer surface with a polychromatic light;

means for capturing light diffracted by the structures on the wafer surface;

means for separating the captured light into a plurality of component wavelengths;

means for creating a plurality of diffractive images of the wafer surface, each image being created at a different component wavelength; and means for analyzing the diffractive images to detect defects in the structures.

16. The system for performing optical inspection of claim 15 wherein the means for illuminating the wafer surface is a polychromatic white light source.

17. The system for performing optical inspection of claim 16 wherein the means for capturing light diffracted by the structures includes a multiple-charged-couple device (CCD) camera mounted in a position to capture the light at a first-order diffraction angle, said camera including a plurality of CCDs that capture light in a plurality of wavelength ranges.

18. The system for performing optical inspection of claim 17 wherein the plurality of CCDs within the camera capture light in the red, green, and blue wavelength ranges of the visible light spectrum.

19. The system for performing optical inspection of claim 18 wherein the means for separating the captured light into a plurality of component wavelengths includes a prism within the multiple-CCD camera, said prism separating the captured light and directing the separated light onto the CCDs.

20. The system for performing optical inspection of claim 19 wherein the means for creating a plurality of diffractive images of the wafer surface includes a digital filter that receives signals from the CCDs and creates a digital diffractive image of the wafer surface.

21. The system for performing optical inspection of claim 15 further comprising a line detector for detecting the component wavelengths across the polychromatic light spectrum.

22. The system for performing optical inspection of claim 15 further comprising means for selecting one of the diffractive images for analysis based upon a grating pitch of the structures on the wafer surface.

* * * * *